United States Patent [19]

Taniguchi et al.

[11] Patent Number: 4,624,613
[45] Date of Patent: Nov. 25, 1986

[54] SELF-SERVICE APPARATUS FOR SERVING FOODS OR DRINKS

[75] Inventors: Harusige Taniguchi, Tokyo; Kyoko Taniguchi, 4-432, Ikebukuro, Toshima-ku, Tokyo, both of Japan

[73] Assignee: Kyoko Taniguchi, Tokyo, Japan

[21] Appl. No.: 664,210

[22] Filed: Oct. 24, 1984

[30] Foreign Application Priority Data

Jul. 28, 1984 [JP] Japan .................... 59-157983

[51] Int. Cl.⁴ .................. A47G 21/00; E04H 3/04; B25J 15/00; B25B 1/00
[52] U.S. Cl. .................................... 414/9; 186/42; 186/49; 74/142; 901/39; 294/100; 221/81
[58] Field of Search .............. 186/42, 38, 49, 50; 221/79, 81, 87, 88, 96, 5, 86; 222/218, 211, 39; 219/214; 74/142; 414/9, 225; 294/100; 901/39, 31

[56] References Cited

U.S. PATENT DOCUMENTS

| | | | |
|---|---|---|---|
| 709,793 | 9/1902 | McGinnity | 222/218 |
| 2,208,298 | 7/1940 | Mahaffey | 221/86 |
| 2,610,767 | 9/1952 | Gardner et al. | 222/39 |
| 2,883,027 | 4/1959 | Jente | 186/38 X |
| 3,189,368 | 6/1965 | Petersen | 74/142 X |
| 3,228,536 | 1/1966 | Gratzer | 414/9 |
| 3,456,817 | 7/1969 | Irazoqui | 221/79 X |
| 3,575,265 | 4/1971 | Simjian | 186/49 |
| 3,840,153 | 10/1974 | Devlin | 222/211 X |
| 3,953,091 | 4/1976 | Shults | 186/49 X |
| 4,162,868 | 7/1979 | Stapleton et al. | 414/9 |
| 4,398,857 | 8/1983 | Layman, Sr. | 414/9 |
| 4,522,543 | 6/1985 | Robinson | 414/9 |

Primary Examiner—Joseph J. Rolla
Assistant Examiner—Gregory L. Huson
Attorney, Agent, or Firm—Darby & Darby

[57] ABSTRACT

A self-service apparatus is provided to be operated by a user for selectively serving foods or drinks. The self-service apparatus includes a support and a cover fixedly supported by the support for covering foods and drinks. A shaft is suspended from the support, and a rotary disk is rotatably mounted on the shaft to be rotated about the shaft upon actuation of a lever. Servers are carried by the rotary disk and hold a food portion or drink. A desired food portion or drink may be selectively served to the user by operating the lever at a desired position.

12 Claims, 6 Drawing Figures ically handicapped persons or partially paralyzed patients or the elderly, must be helped by nurses or attendants when they want to take foods or drinks. It takes much time and labor to supply such a disabled person with means. However, there has not been developed a convenient self-service apparatus which may be operated by such a disabled person to help himself to take a desired food or drink.

SELF-SERVICE APPARATUS FOR SERVING FOODS OR DRINKS

BACKGROUND OF THE INVENTION

1. Field of the Invention

The present invention relates to a self-service apparatus for serving foods or drinks, and particularly to such a self-service apparatus which may be operated by those who are partially paralyzed or physically handicapped to be confined to bed by handling a lever directly or indirectly by any of movable parts, such as hand, arm, foot, leg or head, to serve a desired food or drink easily by themselves.

2. Prior Art

In the past, disabled persons who are lying on beds, such as physically handicapped persons or partially paralyzed patients or the elderly, must be helped by nurses or attendants when they want to take foods or drinks. It takes much time and labor to supply such a disabled person with means. However, there has not been developed a convenient self-service apparatus which may be operated by such a disabled person to help himself to take a desired food or drink.

OBJECTS AND SUMMARY OF THE INVENTION

A primary object of this invention is to provide a self-service apparatus which may be operated simply by any movable part of a person who is lying on a bed to serve a desired food or drink to the neighbourhood of the mouth of the person.

Another object of this invention is to provide a self-service apparatus for serving a desired food or drink to a disabled patient who is lying on a bed, the apparatus being simple in construction without the need of incorporation of complicated electronic instruments.

A further object of this invention is to provide such a self-service apparatus which has simple mechanism and can be manufactured at a low cost.

The above and other objects of this invention will become apparent from the following description of the invention.

The self-service apparatus for selectively serving foods or drinks, according to the present invention, comprises support means, a cover fixedly suspended from said support means to cover foods and drinks, a shaft connected to and extending from said support means, a rotary disk mounted on said shaft for rotating about said shaft, operable means for rotating said rotary disk, and a plurality of server means arranged at the periphery of said rotary disk for carrying thereon said foods and drinks, said operable means being actuated by a user to rotate said rotary disk and said server means until said rotary disk is stopped at a desired position to serve a selected food or drink.

PREFERRED EMBODIMENT OF THE INVENTION

A preferred embodiment of the invention will now be described with reference to the appended drawings.

Figure 1:
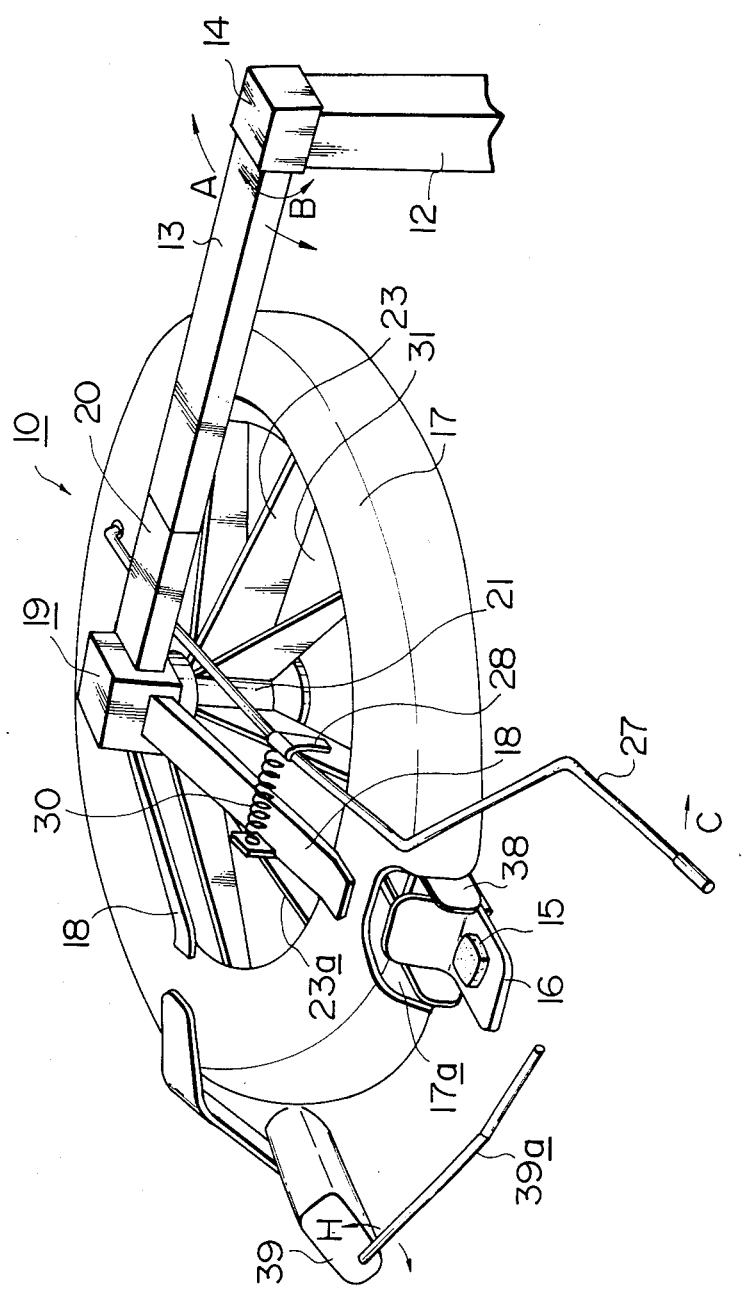
FIG. 1 is a perspective view of a self-service apparatus according to the invention.
Figure 2:
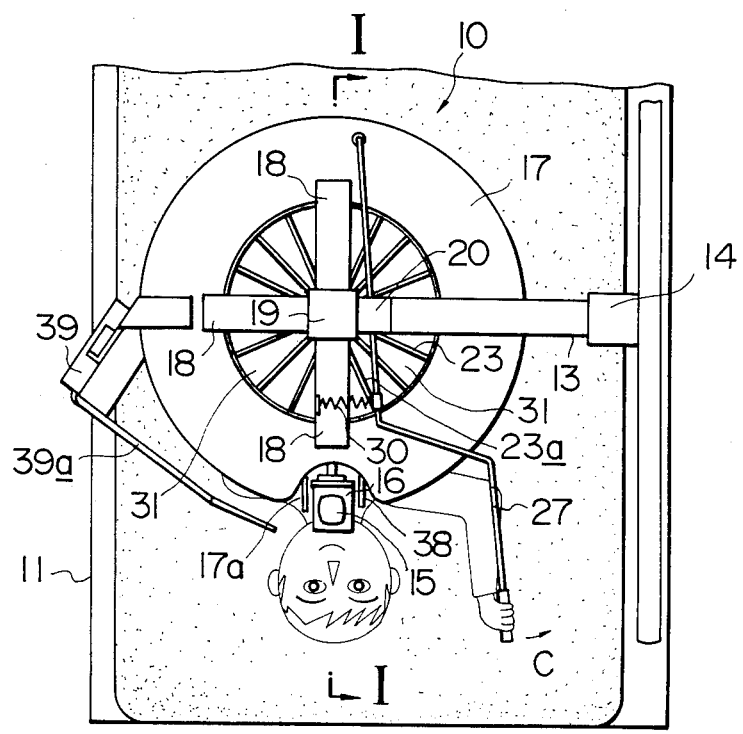
FIG. 2 is a plan view of the self-service apparatus shown in FIG. 1.
Figure 3:
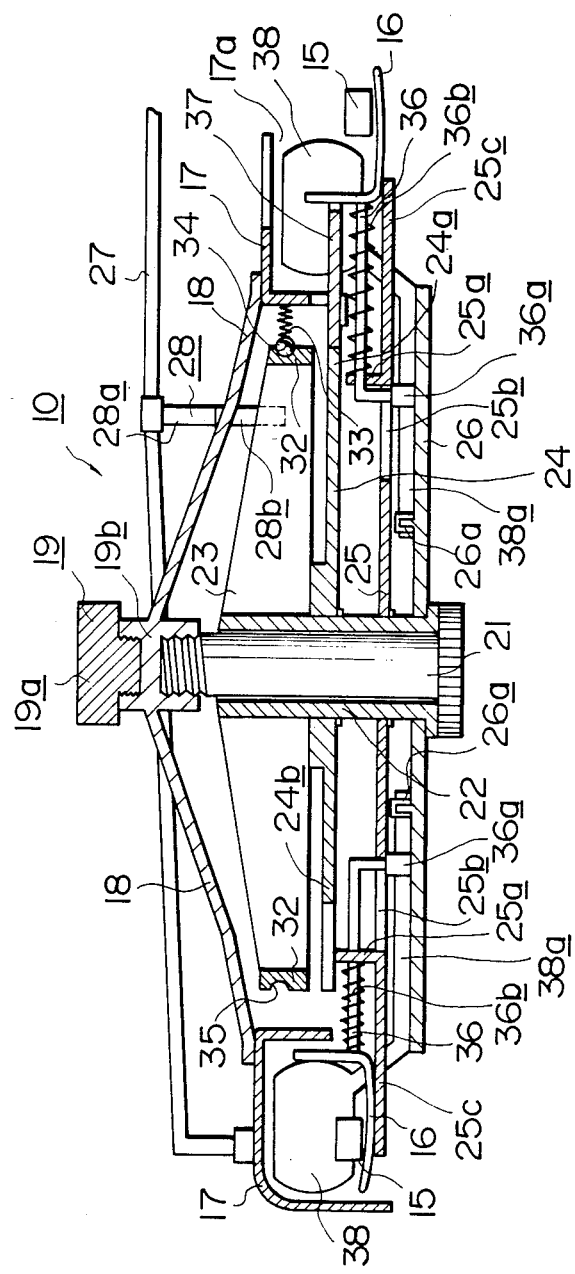
FIG. 3 is a sectional view taken along line I—I of FIG. 2.

A self-service apparatus according to the present invention is generally denoted by reference numeral 10 in FIGS. 1 to 3. The self-service apparatus 10 is placed by or mounted to the side of a bed by means of a vertical stand 12 to which a support member 13 is connected through a universal joint 14 and extends substantially in the horizontal plane. The self-service apparatus 10 is suspended from the support member 13. The universal joint per se is well-known in the art, and will not be described in detail herein. Since the support member 13 is linked through the universal joint 14 with the vertical stand 12, the support member 13 can be swung in the horizontal plane as shown by the arrows A and also can be rotated as shown by the arrows B (FIG. 1), so that the self-service apparatus 10 may be arbitrarily moved in the horizontal plane to a desired position and then tilted to facilitate easy access by the user.

The apparatus 10 has an annular cover 17 for covering a plurality of servers 16 on which foods 15 are held. The annular cover 17 is fixedly connected to a center support member 19 through radial beams 18. A support arm 20 is secured to the center support member 19 to be detachably connected to the support member 13. The self-service apparatus 10 may be disassembled from the support member 13 for cleaning or other purposes simply by disconnecting the support arm 20 from the support member 13. The foods 15 may be placed on tableware (not shown) or substituted by drinks contained in suitable containers.

As best seen from FIG. 3, the center support member 19 includes an upper support member 19a and a lower support member 19b fixed to the upper support member 19a by means of a screw. A center shaft 21 is screwed to the lower support member 19b. The support members 19a and 19b and the cover 17 fixed to the member 19b through the radial beams 18 may be readily disassembled from the other parts of the apparatus 10 to be ready for cleaning.

As seen from FIGS. 1 to 3, a rotary sleeve 22 is mounted on the center shaft 21 for free rotation about the shaft 21. A cam disk 24 provided with a plurality of partition walls or hubs 23 is fixed to the sleeve 22 to be rotated with the sleeve 22 as will be described in detail hereinafter. A rotary disk 25 for carrying thereon the servers 16 is fixed to the sleeve 22 at a distance below the cam disk 24 to be rotated with the sleeve 22. At the lower end of the rotary sleeve 22, a lower carrier disk 26 is fixed to the sleeve to be rotated with the sleeve 22. As described hereinabove, the cam disk 24, rotary disk 25 and the lower carrier disk 26 are integrally connected to the rotary sleeve 22 to be rotated together.

Figure 4:
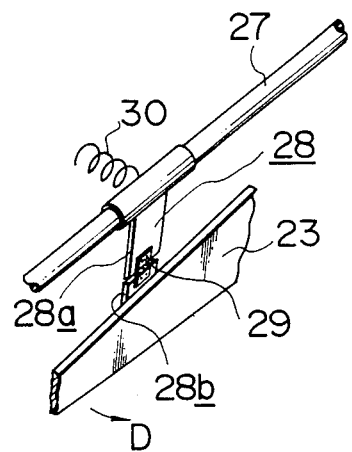
FIG. 4 is a fragmentary perspective view, partly broken away, of the operable lever of the self-service apparatus of the invention.

Referring to FIGS. 1 and 2 in combination, an operation lever 27 is pivoted to the annular cover 17. When the lever 27 is moved by a user in the direction shown by the arrow C, a latch member 28 (FIG. 1) secured to the lever 27 engages with one of the hubs or partition walls 23 to rotate the cam disk 24, the rotary disk 25 and the lower carrier disk 26 fixed to the rotary sleeve 22 simultaneously. As shown in FIG. 4, the latch member 28 includes a base segment 28a and a tongue segment 28b connected through a hinge 29 to the base segment 28a. Since the hinge 29 is foldable only in one way, the tongue segment 28b engages with the hub 23 to rotate the cam disk 24 in the direction shown by the arrow D. The disk 24 cannot be rotated in the reverse direction as the tongue segment 28b is folded by the hinge 29. As a hub 23 is pushed in the direction shown by the arrow D by moving the lever 27 in the direction shown by the arrow C (FIGS. 1 and 2), the latch member 28 engages with the next hub 23a (FIGS. 1 and 2), whereupon the tongue segment 28b is folded to allow the latch member 28 to get over the next hub 23a. If it is desired to rotate the disks 24, 25 and 26 further, the next hub 23a is pushed by the latch member 28. The lever 27 is biased by a spring 30 having one end fixed to one of the radial beams 18 to be returned to a normal rest position.

A ring-shaped peripheral wall 30 (FIG. 3) is welded or otherwise secured to the outer ends of the hubs 23. A plurality of generally hemispherical recesses 35 for receiving a ball member 34 attached to one end of a spring 33 is formed on the outer surface of the peripheral wall 30, one for each segment 31 divided by the hubs or partition walls 23. As the lever 27 is operated to rotate the disk 24 and to allow the latch member 28 to get over one hub 23, the ball member 34 is received by the corresponding recess 35 to stop the rotation.

Figure 5:
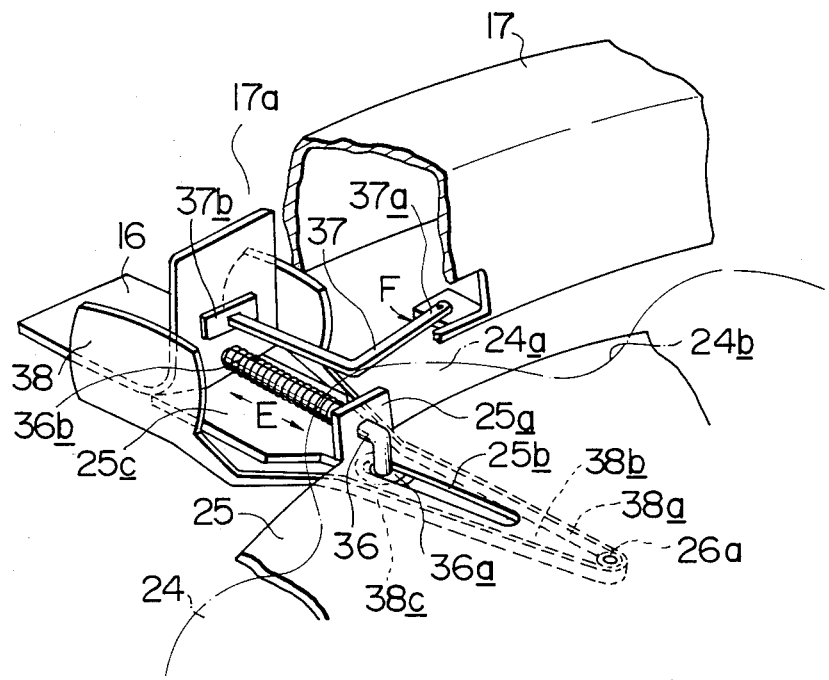
FIG. 5 is a fragmentary perspective view, partly broken away, of the pusher means of the self-service apparatus of the invention.

Referring to FIGS. 3 and 5, a plurality of server means 16, one for each of the segments 31, is carried by a corresponding flanged carrier plate 25c supported by the rotary disk 25. Each server 16 is connected to one end of a push bar 36 which extends through an opening of the flange 25a of the carrier plate 25c, so that each server 16 may be slided in the radial direction (the direction shown by the arrows E in FIG. 5) when it is pushed. The other end of the push bar 36 is angled, as shown, and extends through a slot 25b extending in the radial direction of the rotary disk 25 to be secured to a pedestal 36a. The pedestal 36a is positioned between the rotary disk 25 and the lower carrier disk 26, and slidable below the slot 25b.

As shown in FIG. 5, the cam disk 24 disposed above the rotary disk 25 has a circumferential face provided with projecting cam faces 24a and concaved portions 24b. A cam follower 37 engages with the cam face of the cam disk 24. The cam follower 37 has one end 37a pivoted to the stationary annular cover 17 and biased in the direction shown by the arrow F in FIG. 5. The cam follower has a shape of angled rod, the other end thereof abutting against the back of the server 16. As the lever 27 is operated to rotate the cam disk 24 to allow the cam follower 37 to engage with the projecting cam face 24a (the position shown in FIG. 5), the cam follower 37 is swung against the action of the bias spring 36b so that the server 16 is pushed outwards by the other end 37b of the cam follower 37. One cam follower 37 is provided at the vicinity of an opening 17a formed through the peripheral wall of the annular cover 17. As the cam disk 24 is rotated together with the rotary disk 25 and the lower carrier disk 26, servers 16 are successively pushed out of the cover 17 onto a position near the mouth of the user.

Figure 6:
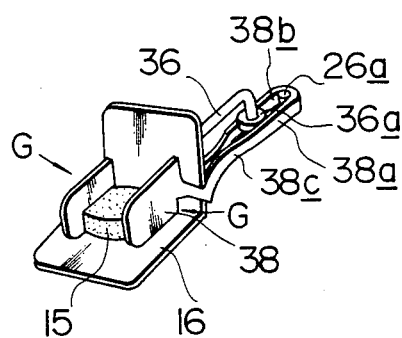
FIG. 6 is a fragmentary perspective view, showing the mechanism, incorporated in the self-service apparatus of the invention, for pinching to hold a food.

As shown in the left half of FIG. 3, the servers 16 other than the one facing to the opening 17a are retracted inwards by the action of the corresponding springs 36b. In this retracted position, the angled end of each push bar 36 engages with the inner end of each slot 25b, and the food 15 placed on each server 16 is pinched by a holder 38, as shown in FIG. 6, to be securely held during the rotational movement. The base 38a of the holder 38 is made of a leaf spring for biasing the pinch ends thereof in the direction shown by the arrows G. The base end of the leaf spring 38a is fixed by a pin 26a so that leg portions 38a of the holder 38 rest on the lower carrier disk 26. Each of the pedestals 36a are positioned in-between the leg portions 38a. When the corresponding server 16 is in the retracted position, the pedestal 36a is fitted in the enlarged slot portion 38b (FIG. 6) so that the food 15 is pinched by the action of the leaf spring. When the corresponding server 16 is pushed outwards in the radial direction, as shown in FIG. 5, at which the angled end of the push bar 36 engages with the outer end of the slot 25b, the pedestal 36a is thrusted in the narrowed portion 38c of the leaf spring 38a so that the pinch ends of the holder 38 are moved in the directions reverse to the arrows G (FIG. 6) to release the food 15 which may be readily taken by the user.

A tank or reservoir 39 for containing a drink may be attached to the annular cover 17, as shown in FIGS. 1 and 2. A tube 39a provided with a mouth piece is pivoted to the tank 39 to be moved upward or downward as shown by the arrow H. The drink contained in the tank 39 is allowed to flow down when the tube 39a is moved downward. In the normal rest condition where the tube is held in the upward position, the drink is prevented from flowing out of the tank.

By the use of the self-service apparatus according to the invention, a desired food or drink can be served by a person who is lying on a bed by simply operating the lever directly or indirectly with any movable parts such as hand, foot or head, without the aid of a nurse or attendant.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A self-service apparatus for selectively serving foods or drinks to those physically handicapped to be confined in bed, which comprises support means, a cover fixedly suspended from said support means to cover foods and drinks, a shaft connected to and extending from said support means, a rotary disk mounted on said shaft for rotating about said shaft, operable means for rotating said rotary disk, a plurality of server means arranged at the periphery of said rotary disk for carrying thereon said foods and drinks, said operable means being actuated by a user to rotate said rotary disk and said server means until said rotary disk is stopped at a desired position to serve a selected food or drink, means for holding said foods or drinks stationary during said rotation of said disk, and releasing means for releasing said foods or drinks when said rotary disk is stopped at said desired position, said holding means including two confronting pinching means movable towards each other by the operation of said releasing means to hold the food and drinks and also movable away from each other by the operation of said releasing means to release said foods or drinks at said desired position.

2. The self-service apparatus according to claim 1 wherein said holding means comprises a holder formed by a leaf spring and said pinching means comprises pinch ends at the end of said holder.

3. The self-service apparatus according to claim 1, wherein said operable means includes a lever operated by a user, latch means fixed to said lever, and hub means extending along the radial direction of said rotary disk to be engaged by said latch means.

4. The self-service apparatus according to claim 3, wherein said latch means includes a base segment fixedly mounted to said lever and a tongue segment connected to said base segment to be folded in one way, said tongue segment being engaged by said hub means.

5. The self-service apparatus according to claim 1, further comprising stopper means for stopping said rotary disk at said desired position.

6. The self-service apparatus according to claim 5, wherein said stopper means include a spring-biased ball member and a peripheral wall having a plurality of generally hemispherical recesses for receiving said ball member, said peripheral wall being rotated together with said rotary disk.

7. The self-service apparatus according to claim 1, further comprising a tank for containing a drink.

8. The self-service apparatus according to claim 7, wherein said tank communicates with a tube having a mouth piece, said tube being pivotably connected to said tank.

9. The self-service apparatus according to claim 1, further comprising pusher means for pushing said server means outwards in the radial direction of said rotary disk at said desired position.

10. The self-service apparatus according to claim 9, wherein said pusher means includes a cam disk which is rotated cooperatively with said rotary disk, and a cam follower for engaging with said cam disk to be moved outwards at said desired position to push said server means outwards in the radial direction of said rotary disk.

11. The self-service apparatus according to claim, 2 wherein said releasing means include a push bar attached to said server means and a pedestal mounted to said push bar, said pedestal being moved outwards in the radial direction of said rotary disk when a selected one of said server means is pushed outwards in the radial direction at said desired position so that said holding means is opened to release said food or drinks as the pedestal is moved to the outermost position.

12. The self-service apparatus according to claim 11, wherein a plurality of said pedestals and said holding means, one set of said pedestal and said holding means for each server means, is carried by a circular carrier disk which is rotated cooperatively with said rotary disk.

* * * * *